United States Patent [19]
Nardella et al.

[11] Patent Number: 5,817,091
[45] Date of Patent: Oct. 6, 1998

[54] ELECTROSURGICAL DEVICE HAVING A VISIBLE INDICATOR

[75] Inventors: Paul C. Nardella, Wareham, Mass.; David C. Yates, West Chester, Ohio

[73] Assignees: Medical Scientific, Inc., Taunton, Mass.; Ethicon Endo-Surgery, Inc., Cincinnati, Ohio

[21] Appl. No.: 859,503

[22] Filed: May 20, 1997

[51] Int. Cl.⁶ .................................................. A61B 17/36
[52] U.S. Cl. .................................. 606/38; 606/35; 606/37
[58] Field of Search .................................. 606/38, 39, 40, 606/48, 49, 50, 35, 37

[56] References Cited

U.S. PATENT DOCUMENTS

| | | | |
|---|---|---|---|
| 2,611,365 | 9/1952 | Rubens . | |
| 2,765,457 | 10/1956 | Stang | 340/253 |
| 3,707,149 | 12/1972 | Hao et al. | 128/303.14 |
| 3,875,945 | 4/1975 | Friedman | 128/303.14 |
| 3,933,157 | 1/1976 | Bjurwill et al. | 606/35 |
| 4,051,855 | 10/1977 | Schneiderman | 128/303.14 |
| 4,092,986 | 6/1978 | Schneiderman | 128/303.14 |
| 4,114,623 | 9/1978 | Meinke et al. | 128/303.14 |
| 4,209,018 | 6/1980 | Meinke et al. | 128/303.17 |
| 4,338,940 | 7/1982 | Ikuno | 128/303.14 |
| 4,416,276 | 11/1983 | Newton et al. | 606/35 |
| 4,474,179 | 10/1984 | Koch | 128/303.14 |
| 4,485,812 | 12/1984 | Harada et al. | 128/303.15 |
| 4,655,216 | 4/1987 | Tischer | 128/303.17 |
| 4,658,819 | 4/1987 | Harris et al. | 128/303.13 |
| 4,706,667 | 11/1987 | Roos | 128/303.14 |
| 4,862,889 | 9/1989 | Feucht | 128/303.13 |
| 4,969,885 | 11/1990 | Farin | 606/38 |
| 5,122,137 | 6/1992 | Lennox | 606/40 |
| 5,133,711 | 7/1992 | Hagen | 606/38 |
| 5,167,660 | 12/1992 | Altendorf | 606/40 |
| 5,190,541 | 3/1993 | Abele et al. | 606/46 |
| 5,207,691 | 5/1993 | Nardella | 606/142 |
| 5,269,780 | 12/1993 | Roos | 606/42 |
| 5,342,357 | 8/1994 | Nardella | 606/40 |
| 5,403,312 | 4/1995 | Yates et al. | 606/50 |
| 5,423,810 | 6/1995 | Goble et al. | 606/40 |
| 5,443,463 | 8/1995 | Stern et al. | 606/51 |
| 5,458,598 | 10/1995 | Feinberg et al. | 606/52 |

FOREIGN PATENT DOCUMENTS

| | | |
|---|---|---|
| WO 9206642 | 4/1992 | European Pat. Off. . |
| WO 9320747 | 10/1993 | European Pat. Off. . |
| 640317A1 | 3/1995 | European Pat. Off. . |
| 2213381 | 8/1989 | United Kingdom . |

*Primary Examiner*—Gary Jackson
*Assistant Examiner*—Julian W. Woo
*Attorney, Agent, or Firm*—Nutter, McClennen & Fish, LLP

[57] ABSTRACT

An electrosurgical system having a visual indicator is provided. In a first embodiment, the electrosurgical system includes an active electrode coupled to a power supply for providing electrosurgical energy from the power supply to a tissue area and a return electrode separated from the active electrode, the return electrode being adapted to receive a current flowing through the tissue. The electrosurgical system further includes a lamp in electrical communication with the active and return electrodes, wherein the neon bulb is illuminated when the current flowing through the tissue exceeds a predetermined threshold. In a further embodiment, the electrosurgical system includes a second lamp illuminated when a voltage through the tissue is greater than a predetermined threshold. In another embodiment, a monopolar electrosurgical device includes a visual indicator for indicating conditions at an area of affected tissue. The visual indicator circuit includes a transformer having a secondary winding, a wire through the transformer forming the primary winding, a series resistor coupled in series with the secondary winding, and a type NE-2 neon bulb coupled in series with the series resistor, wherein the lamp is illuminated when the current through the wire is greater than a predetermined threshold.

18 Claims, 7 Drawing Sheets

ELECTROSURGICAL DEVICE HAVING A VISIBLE INDICATOR

CROSS REFERENCE TO RELATED APPLICATION

Not applicable.

STATEMENT REGARDING FEDERALLY SPONSORED RESEARCH

Not applicable.

BACKGROUND OF THE INVENTION

Surgical procedures often require incisions to be made in human tissue. Such procedures typically require the application of force to a surgical tool having one or more sharp, tissue-contacting edges, and usually create bleeding at the site of the incision. The ease with which the tool makes the incision and the prompt control or elimination of the bleeding thereby created is of paramount importance to the success and safety of the procedure.

Electrosurgical devices utilize electrical current in the form of radio frequency (RF) energy to incise and to cauterize tissue to control bleeding. U.S. Pat. No. 4,651,734 discloses a surgical scalpel modified to include an electrode. This scalpel has the ability to cut tissue and, when properly positioned, to cauterize tissue following a cutting procedure.

Some surgical tools which employ RF energy to cut and cauterize do so with a constant energy supply. Because of this, the tool must be carefully controlled during surgery to ensure that the correct amount of RF energy is applied to the target tissue. For example, if a surgical tool delivers RF energy through a cutting edge to tissue at a magnitude sufficient to cut or cauterize tissue, tissue burns could result if the cutting edge contacts the tissue for too long a period. Similarly, if the cutting edge is moved too quickly through tissue, the optimal amount of energy may not be applied to the tissue. Thus, if not used properly, electrosurgical tools may not take full advantage of the benefits of electrosurgery.

Other electrosurgical devices measure the impedance of tissue to be affected as a feedback parameter to maintain the impedance of the tissue within predetermined limits by controlling the level of electrosurgical energy. By controlling the level of electrosurgical energy applied to a tissue area, the electrosurgical device allows simultaneous cutting and cauterization of tissue independently of a user's technique.

Some electrosurgical tools have digital display units or bar graph displays for indicating power, voltage and other parameters relating to electrosurgical device operation. Such displays often provide a theoretical value and not a value measured at a relevant tissue area. While these displays might provide some information, actual measurements of the affected tissue are necessary in order to allow a user to most effectively cut and cauterize tissue during an electrosurgical procedure. Furthermore, such graphical displays require a user to focus attention on the display for an amount of time necessary to ascertain a display reading and process that information.

Still other electrosurgical devices provide an audible alarm which sounds when a theoretical energy level is exceeded, thus not providing information from an affected tissue area. Also, as one skilled in the art will appreciate, an audible alarm may be confused with other equipment having sounds associated therewith, such as cardiac and respiratory monitors. Furthermore, the number of audible sounds which a user can easily and unambiguously assimilate is limited, and multiple sounds corresponding to various information could be quite confusing to a user. Often, music is played in surgical procedure areas, thus adding further uncertainty to perceived audible signals. A further disadvantage to an audible signal is that if a signal is missed, a user cannot utilize the information provided by the signal unless the audible signal is repeated.

SUMMARY OF THE INVENTION

The present invention overcomes the aforesaid and other disadvantages by providing an electrosurgical system having an easily monitored, unambiguous visible indicator for indicating conditions at an area of tissue to be affected. The visible indicator is useful with a variety of electrosurgical devices, such as impedance feedback cutting and coagulating systems and surgical clip applying devices.

In a first embodiment in accordance with the present invention, an electrosurgical system having a visual indicator includes an active electrode coupled to a power supply, and a return electrode electrically separated from the active electrode, the return electrode being adapted to receive a current flowing from the active electrode. The visual indicator includes a lamp in electrical communication with the active and return electrodes, wherein the lamp is illuminated when the current exceeds a predetermined threshold.

In another embodiment, the electrosurgical system includes a lamp that is illuminated when a voltage across the active and return electrodes is greater than a predetermined threshold.

In a further embodiment, a monopolar electrosurgical instrument includes a visible indicator having a toroid type transformer with a primary winding passing through the transformer, and a lamp which is illuminated when the current through the wire is greater than a predetermined threshold.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a visible indicator for use with an electrosurgical system, such as an impedance feedback electrosurgical system. The visible indicator provides an indication of conditions at an area of affected tissue to a user thereby enabling the user to more effectively cut and cauterize tissue.

Figure 1:
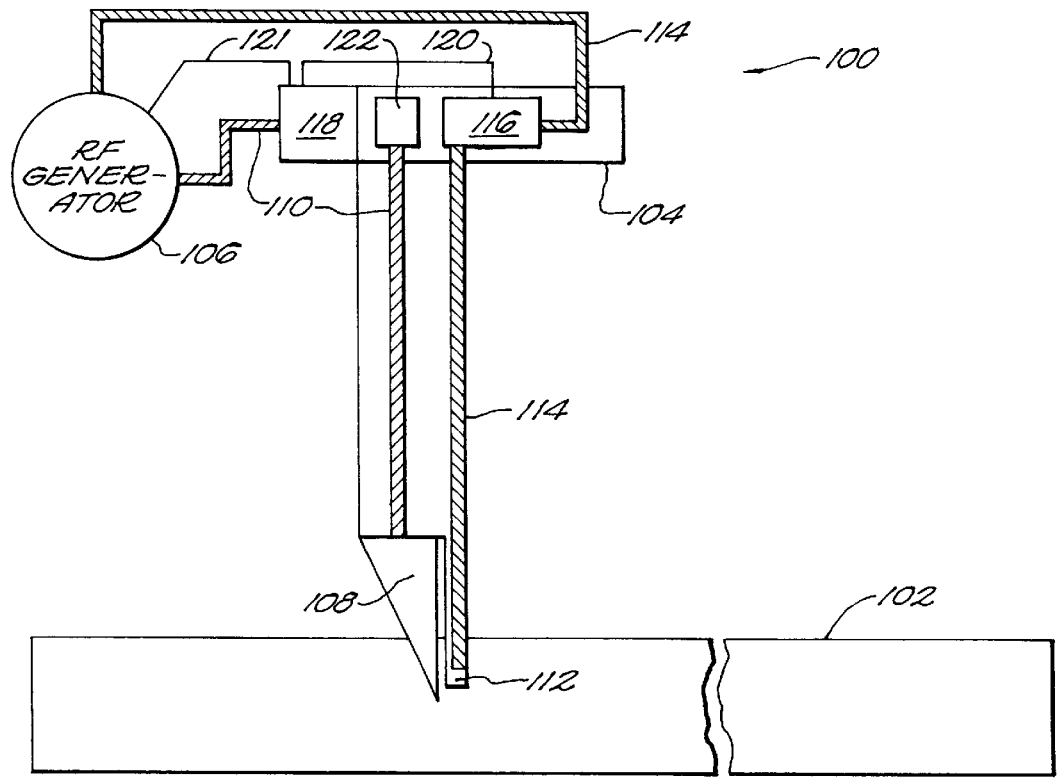
FIG. 1 schematically illustrates a prior art impedance feedback electrosurgical system.

FIG. 1 illustrates an exemplary prior art impedance feedback electrosurgical system 100 in use with an electrosurgical tool 104. The system 100 includes an electrosurgical tool 104 which is connected in circuit to a power source, shown preferably as an RF generator 106. The tool 104 has an active electrode 108 which operates as a cutting edge and delivers electrosurgical energy to tissue 102. The active electrode 108 is connected to a first pole of the electrosurgical energy supply, illustrated as an RF generator 106, through a power supply line 110. A return electrode 112 is also associated with the tool 104 and is connected to a second pole of the electrosurgical supply 106 via a return line 114. An impedance monitor 116—preferably having a programmable CPU—connects in circuit with the electrodes 108 and 112 to measure tissue impedance and to generate a signal representative of tissue impedance which is conveyed to a power control module 118 through a signal line 120. The power control module 118 regulates the electrosurgical energy generated from the RF generator 106 through a control line 121 such that the impedance measured by the impedance monitor 116 remains within a preselected range. Moreover, the system preferably includes an activation switch 122 which a user can selectively operate to control the flow of energy to the delivery electrode 108.

In operation, force can be applied to the tool 104 when the active electrode 108 contacts the tissue 102 to make an incision. Electrosurgical energy applied through tool 104 heats the cells in contact with the electrodes to provide a clean incision. In the course of cutting, the electrosurgical energy applied through the tool 104 also cauterizes tissue to minimize or eliminate any associated bleeding. Without the delivery of electrosurgical energy, e.g., RF energy, through the active electrode 108, the surgical incision would be less effective and hemostatic as it would rely solely on the mechanical sharpness of the cutting blade.

As noted, tissue impedance is maintained within a preselected range. Upon delivery of electrosurgical energy to tissue 102 through the active electrode 108, current through and voltage across the tissue is measured for use by an impedance monitor 116, where tissue impedance is determined. Accordingly, as the amount of tissue that contacts the active electrode 108 is altered, the current at the return electrode 112 changes. The impedance monitor measures this change in tissue resistance (i.e., impedance) and conveys a signal representative of the measured impedance to the control module 118, which in turn makes any necessary increase or decrease in the energy (shown here as voltage) conveyed to the active electrode to maintain tissue impedance within a desired range. Preferably, this electrosurgical energy is in the radio frequency range of 200 KHz to 3 MHz, and the tissue impedance ranges between about 10 and 500 Ohms.

Figure 2:
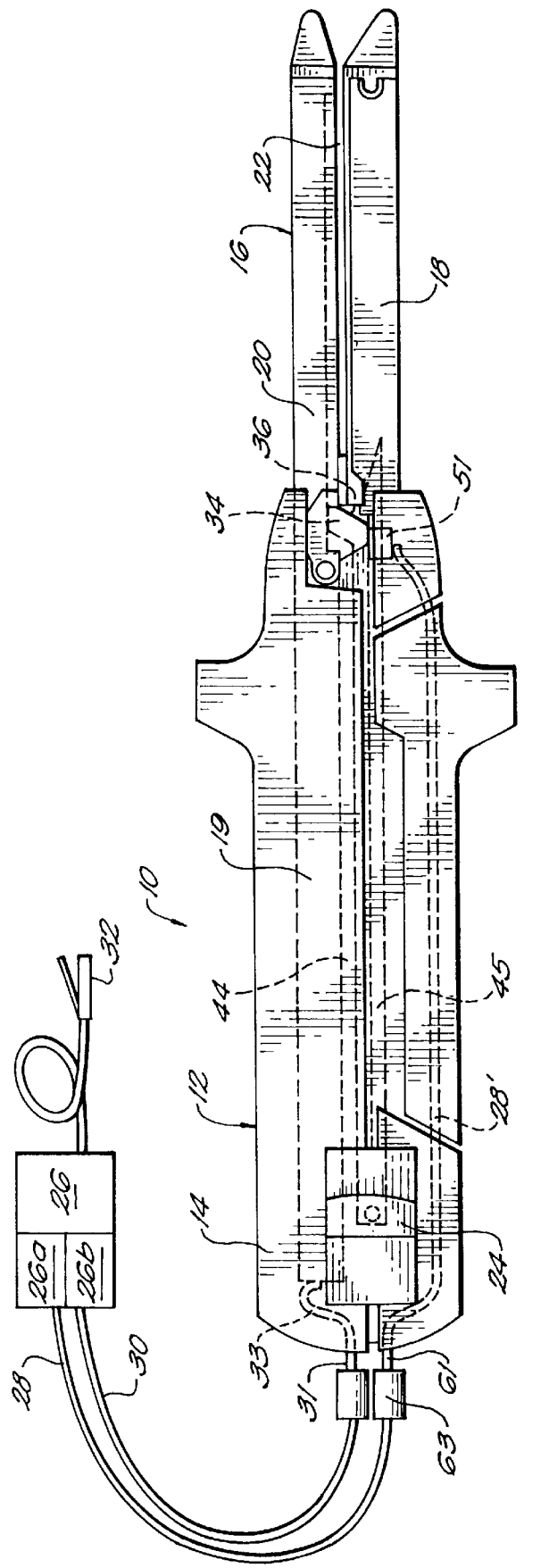
FIG. 2 schematically illustrates a prior art surgical cutting tool employed in the impedance feedback electrosurgical system of FIG. 1.

FIG. 2 illustrates an illustrative embodiment of a prior art electrosurgical cutting tool 10 used with the impedance feedback system of FIG. 1. Cutting tool 10 is a linear cutting tool comprising a housing 12 including a handle portion 14. Adjacent handle portion 14 is cutting template element 16 which includes a first tyne 18 and a second tyne 20. The two tynes 18, 20 of cutting template element 16 are substantially parallel and define a tissue engaging space 22 into which is inserted the tissue or organ to be incised. In a preferred embodiment, the surgical tool 10 includes a lever 24 which facilitates the movement of an active electrode, which may take the form of a cutting blade 34, along a predetermined path.

An electrosurgical generator 26 serves as an energy source from which electrical current, preferably in the radio frequency range, is communicated to the cutting tool through insulated wire 28 and connector 63. Insulated wire 30 communicates through connector 31 and return wire 33 to a conductive portion of tyne 20 which serves as the ground or return electrode. A power switch 32, preferably in the form of a foot petal, may be used to break or close the generator 26 circuitry and thus inhibit or transmit the power supplied to the cutting tool. Alternatively, a power switch may be disposed on a portion of the cutting tool such as the housing 12.

The circuit representing the power generator 26, the active electrode (e.g., blade 34), the return wire electrode, and the control module 26a, and impedance monitor 26b is electrically isolated to control the application of surgical energy by the tool. The control module 26a can regulate the electrosurgical energy delivered to the cutting blade 34, according to the measured tissue impedance determined by the impedance monitor 26b. As noted, the impedance monitor generates a signal representative of tissue impedance by quantifying the current received at the return electrode, which is a conductive portion of the tyne 20, and the voltage across the electrodes. The tissue impedance signal is communicated to the control module which in turn adjusts the applied electrosurgical energy to maintain a measured tissue impedance within a preselected range. Accordingly, electrosurgical energy adjustments are made automatically to maintain a skin or tissue impedance to within a safe and operable range, independent of the speed and operator technique in using the tool 10.

The energy requirements of the electrosurgical tool are dynamic and depend to a great extent upon the impedance values of the tissue encountered by the active electrode, e.g., blade 34, during cutting procedures. The impedance of tissue varies among tissue types and the amount of blood present in or around the tissue. The amount of current delivered by the tool to the tissue is a function of generator power output and the impedance of the tissue. Where tissue contacted has a lower impedance value, more electrosurgical current will be delivered to the blade 34 by operation of the impedance monitor 26b and control module 26a, and, conversely, less electrosurgical current will be delivered to the blade 34 when the tissue has a higher impedance value. Generally, the amount of current delivered to tissue ranges between about 0.1 and 2.0 amps. The voltage applied to the tissue between the blade and the return electrode typically is between about 20 to 200 volts rms. These values are typical and are varied automatically to maintain a nearly constant current in the tissue during operation of the tool 10.

Figure 3A:
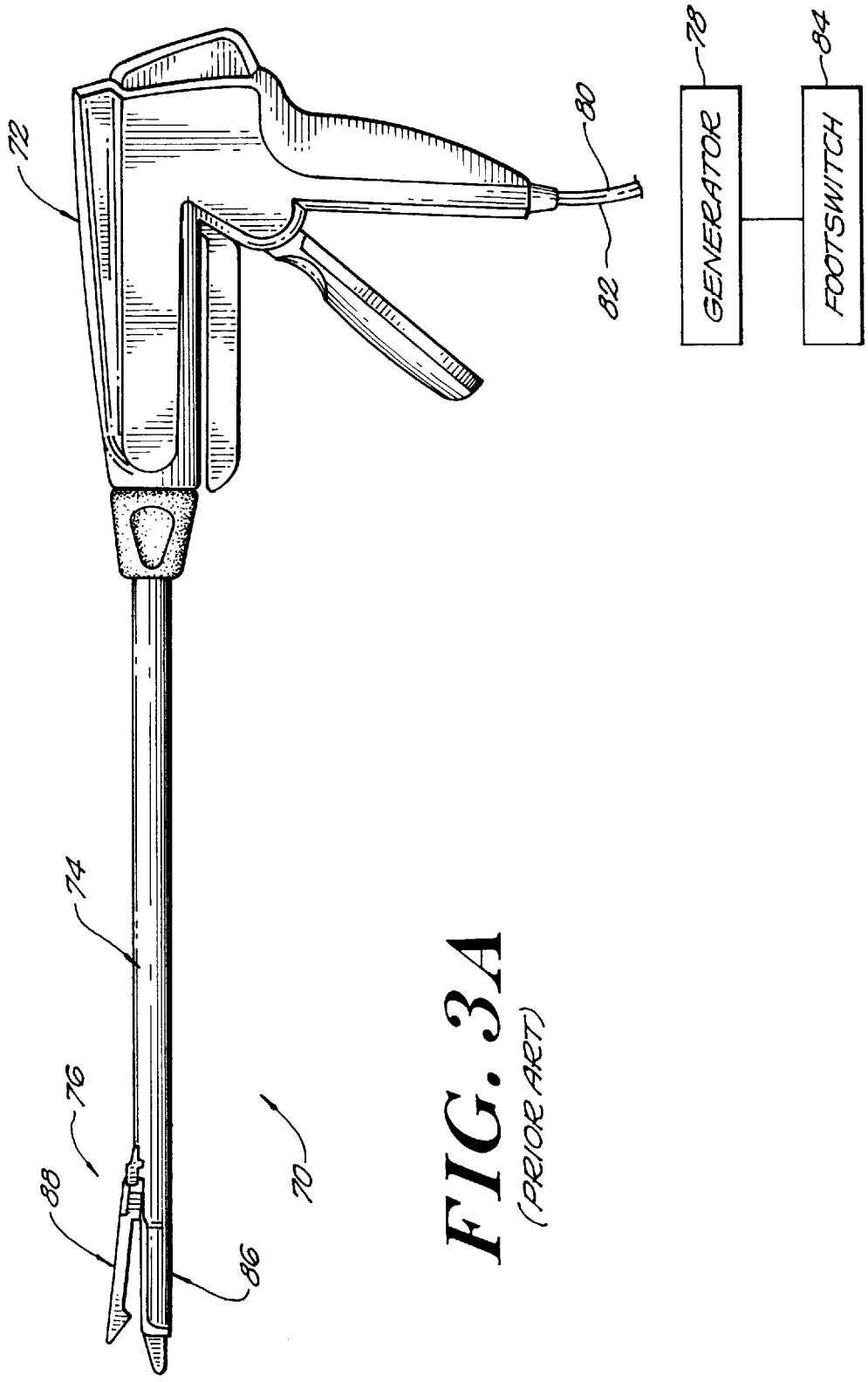
FIG. 3A schematically illustrates a further prior art impedance feedback electrosurgical system.

FIG. 3A illustrates an exemplary prior art impedance feedback electrosurgical system in use with an electrosurgical tool further shown and described in U.S. Pat. No. 5,403,312 to Yates, incorporated herein by reference. The electrosurgical tool is in the form of an electrocautery linear cutting and stapling instrument 70 including a body 72 coupled to a shaft 74 coupled to an end effector 76 for affecting tissue. Bipolar electrosurgical energy is supplied to the end effector 76 from an electrosurgical generator 78 through wires 80,82 extending into the body 72 of the instrument under the control of a footswitch 84. The instrument 70 measures current through and voltage across the tissue in contact with jaws 86,88 of the end effector 76 so that the impedance of tissue can be derived. The instrument 70 maintains the tissue impedance within a preselected range.

Figure 3B:
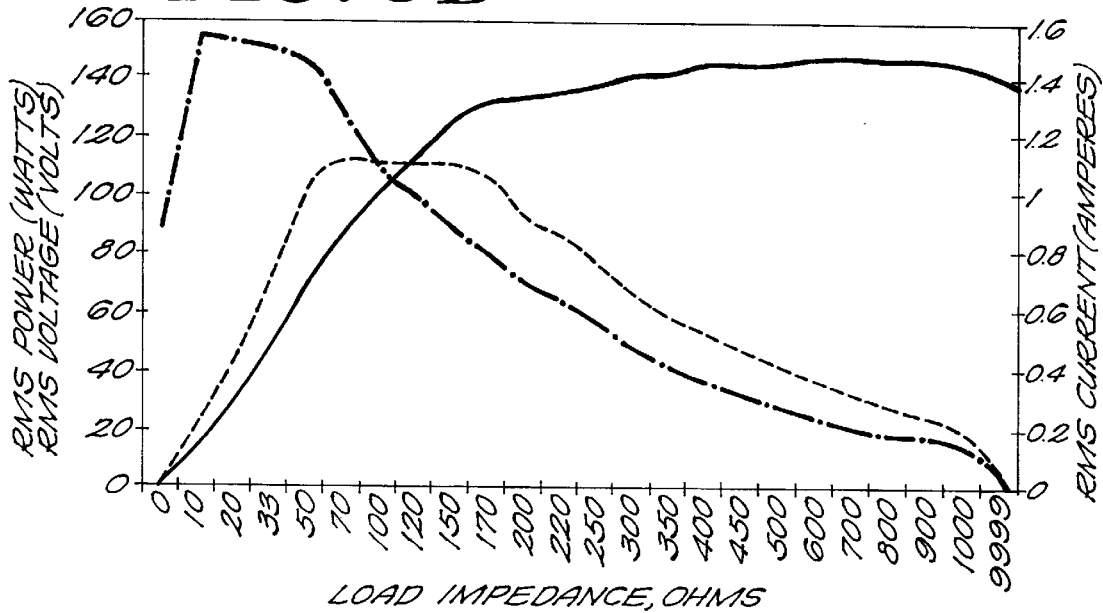
FIG. 3B is a graphical representation of a load curve associated with a generator forming a portion of the electrosurgical system of FIG. 3A.
Figure 3C:
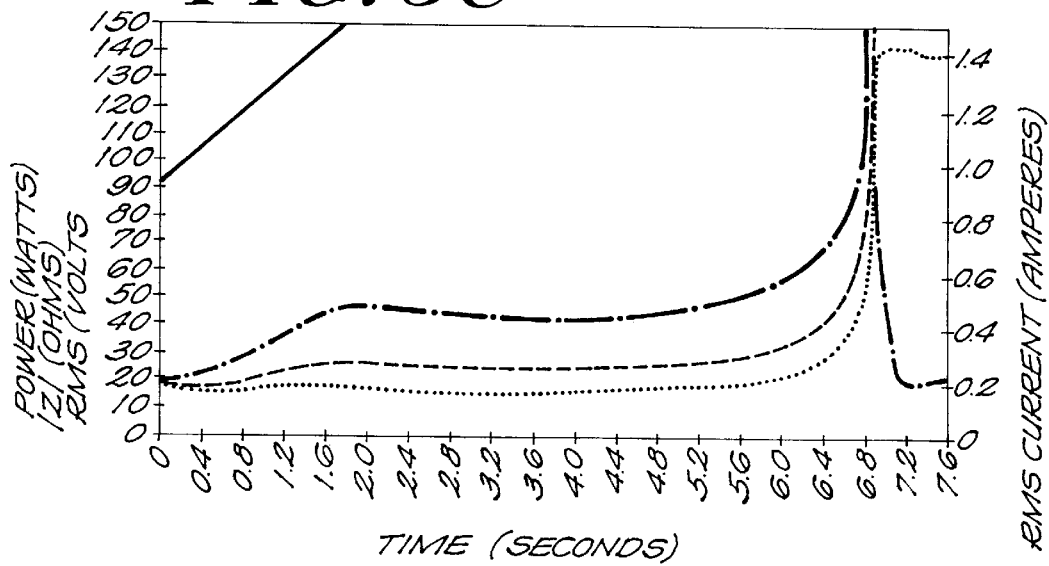
FIG. 3C is a typical coagulation episode.

FIG. 3B illustrates a load curve for an exemplary electrosurgical generator 78 (FIG. 3A), and more particularly, an ERBE ICC350 generarator set to 120 Watts. The load curve illustrates the generator output in response to varying resistive loads with the resulting average power 90, voltage 91, and current 92 being graphically represented. FIG. 3C is a graph of a typical coagulation episode over time for the exemplary generator of FIG. 3B showing voltage 93, current 94, power 95, and tissue impedance 96. The tissue impedance seen by the instrument remains relatively constant over time as the tissue coagulates for a given range of applied power. It is understood by one of ordinary skill in the art that excessively high applied power will cause an unpredictable tissue response and that a very low applied power will cause slow, if any, coagulation of the tissue. A dramatic rise 97 in the tissue impedance occurs as collagens and water in the tissue change phase. The rise 97 in impedance results in the applied current decreasing due to the load curve of the generator. The further application of electrosurgical energy to the tissue with the illustrated device will not cause any further significant change in the tissue. By contrast, it should be noted that the application of additional electrosurgical energy in prior art devices can cause tissue damage.

In particular, for radio frequency energy, an exemplary operating range of measured tissue impedance is between 10 and 500 Ohms. As can be seem from the illustrative load curve of FIG. 3B, for a load of greater than about 500 Ohms the current is less than about 300 mA. When operating in this range, tissue incisions occur with effective cell heating, and the tissue is cauterized, without burning, to prevent or minimize bleeding.

Figure 4:
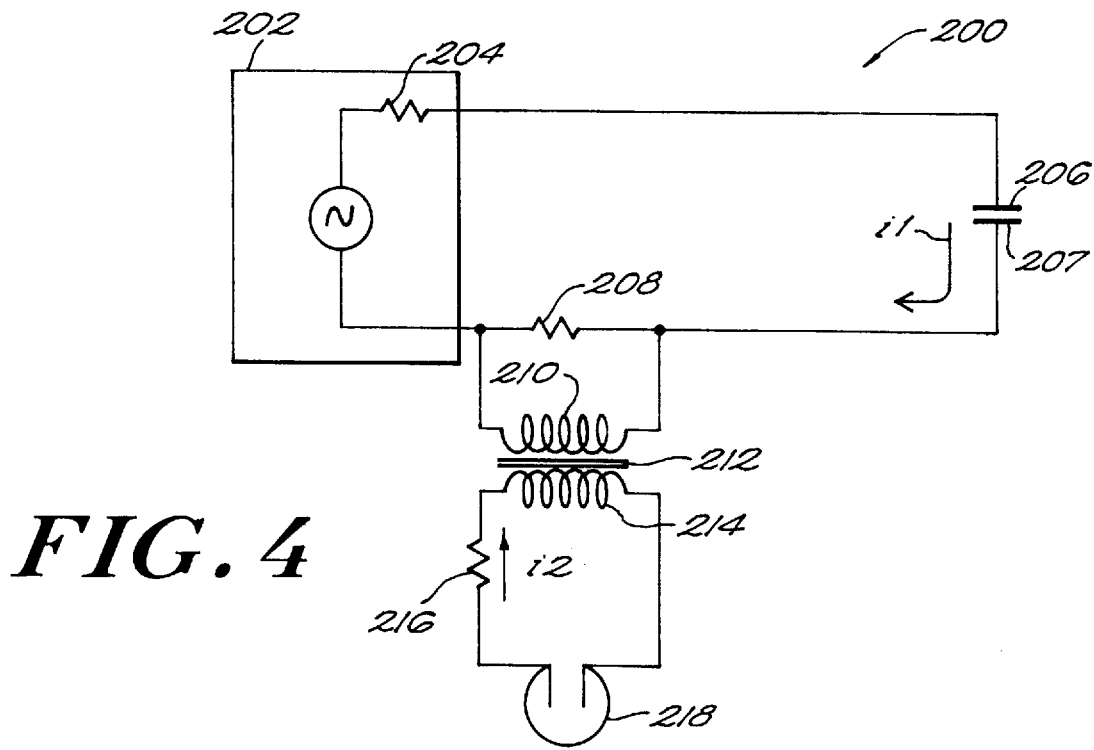
FIG. 4 is a schematic diagram of an indicator circuit in accordance with the present invention adapted for use with the electrosurgical systems of FIGS. 1–3.

FIG. 4 is a schematic diagram of a first embodiment of a visual indicator circuit 200 adapted for use with electrosurgical systems and tools, such as those shown in FIGS. 1–3 respectively. The indicator circuit 200 includes a signal generator 202 having a source impedance 204 coupled in series with an active electrode 206 and a return electrode 207 and a sense resistor 208. A first winding 210 of a step-up transformer 212 is connected to the sense resistor 208 and a second winding 214 of the transformer is connected to a series coupled series resistor 216 and a type NE-2 neon bulb 218.

In operation, the signal generator 202 energizes the indicator circuit 200 with RF energy so that the active electrode 206 can operate on tissue, for example cut and cauterize the tissue. A first current oil flows through the sense resistor 208 as a function of the impedance of tissue between the active and return electrodes 206,207 providing a first voltage across the first winding 210 of the transformer. A stepped up second voltage is induced across the second winding 214 of the transformer 212. The secondary voltage appears across resistor 216 and the neon bulb 218 to light the bulb when the current oil through the tissue is greater than a predetermined threshold. It will be appreciated that the circuit and component values are illustrative and not limited thereto.

Figure 4A:
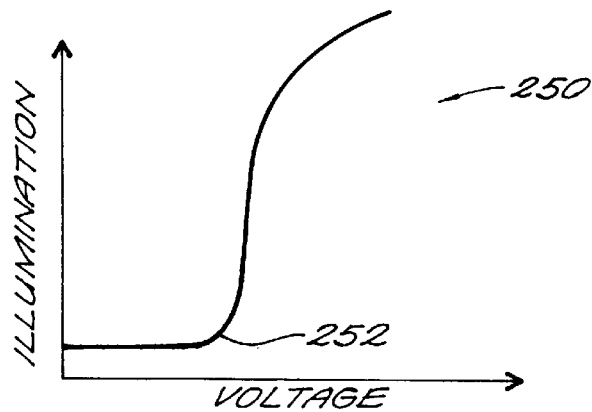
FIG. 4A is a graphical representation of a performance curve for an exemplary type NE-2 neon bulb forming a portion of the indicator circuit of FIG. 4.

A graphical representation 250 of light and voltage for a typical type NE-2 neon bulb is illustrated in FIG. 4A. The voltage illumination graph 250 includes a knee 252 indicating when the bulb is turned on. The knee location is dependent upon the particular neon bulb selected. As can be appreciated by one skilled in the art, the circuit and bulb threshold of illumination can be adjusted by selecting various bulbs having knees at differing voltage levels as well as varying the turns ratio of the transformer, and the sense and series resistor values. Type NE-2 neon bulbs illuminate at a wide range of frequencies including frequencies associated with electrosurgery.

Figure 5:
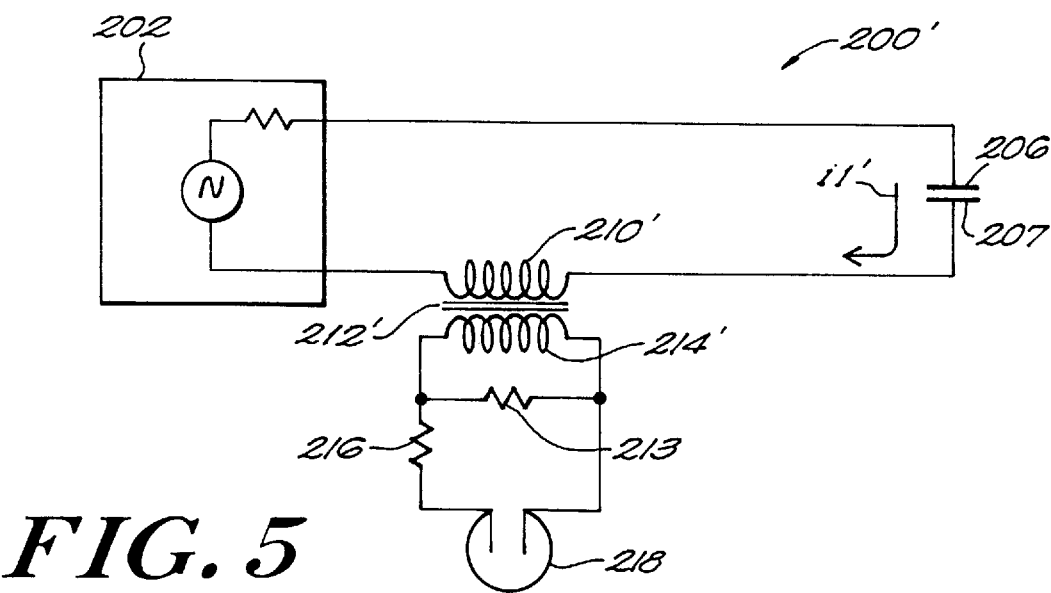
FIG. 5 is a schematic diagram of a further embodiment of the indicator circuit of FIG. 4.
Figure 6:
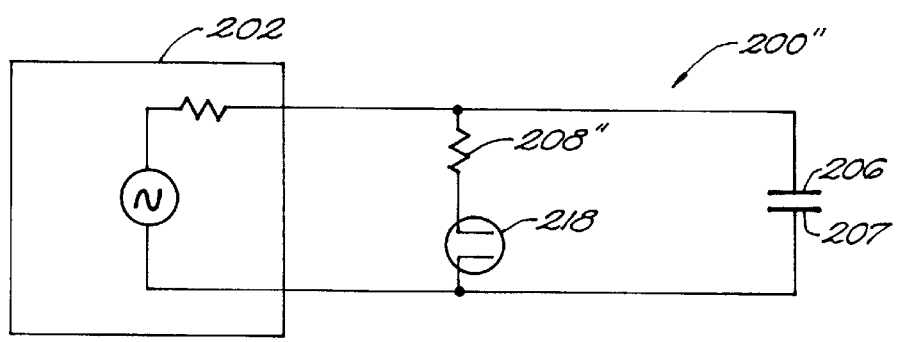
FIG. 6 is a schematic diagram of another embodiment of the indicator circuit of FIG. 4.
Figure 7:
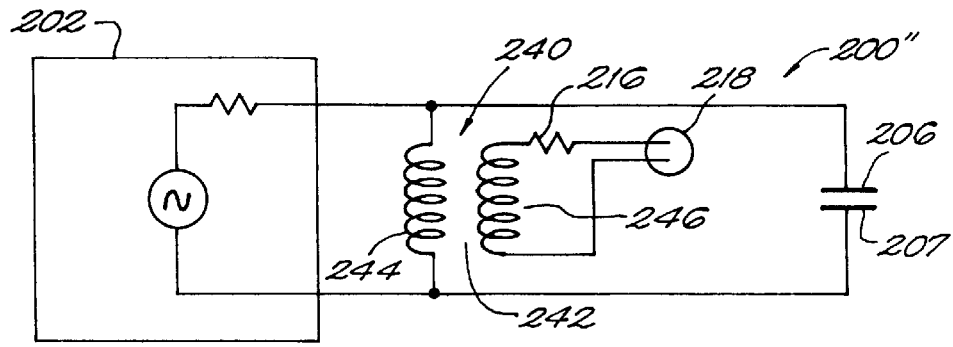
FIG. 7 is a schematic diagram of yet another embodiment of the indicator circuit of FIG. 4.

FIGS. 5–7 are schematic diagrams of alternative embodiments of the indicator circuit of FIG. 4. In FIG. 5, circuit 200' includes a signal generator 202 coupled in series with electrodes 206,207 and a first winding 210' of a step-up transformer 212' having a current i1' flowing through a tissue load. A second winding 214' of the transformer 212' is coupled to a ballast resistor 213 and a series resistor 216 and a type NE-2 neon bulb 218 coupled in series. The neon bulb 218 is illuminated when the current i1' through the tissue load is greater than a predetermined threshold. The indicator circuit 200' of FIG. 5 obviates the need for the sense resistor of FIG. 4 by matching the neon bulb 218 and the ballast resistor 213 to the transformer 212'.

Figure 5A:
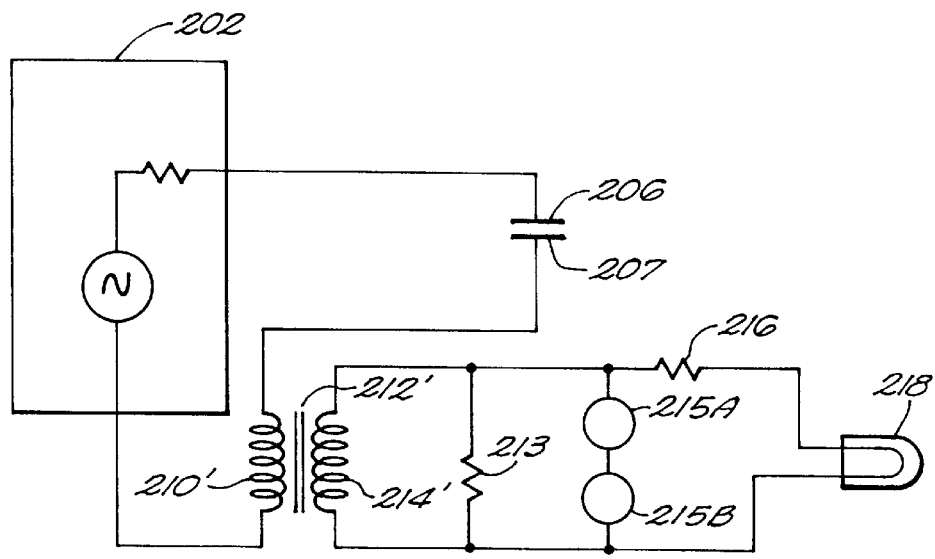
FIG. 5A is schematic diagram of an alternative embodiment of the indicator circuit of FIG. 5.

FIG. 5A includes optional first and second voltage surge protectors 215A,215B coupled in series across the ballast resistor 213. In an exemplary embodiment, the transformer 212' is a 1:75 toroid type transformer having a high pertinacity ($\mu_R$>2000), the ballast resistor 213 is about 70 kΩ and can be coupled in series with a potentiometer, and the series resistor 216 is about 68 kΩ. The resistance of the potentiometer can be adjusted in response to variations in the transformer and/or bulb.

In operation, the ballast resistor 213 sets a current to voltage ratio which sets the current level which will illuminate the indicator lamp 218 and the series resistor 216 limits the current to the lamp. The first and second surge voltage protectors 215A,215B clamp the voltage at the secondary winding 214' of the transformer 212' to prevent saturation of the transformer due to a high secondary voltage. This arrangement also prevents excessive heating of the toroid which can disturb the illumination threshold of the lamp 218, and limits the maximum voltage across the series resistor 216 and lamp 218.

FIG. 6 illustrates indicator circuit 200" for illuminating neon bulb 218 when a voltage in a tissue load is greater than a predetermined level. The voltage indicator circuit 200" includes signal generator 202 and electrodes 206,207 coupled in parallel with a series coupled series resistor 208" and neon bulb 218. The neon bulb 218 is illuminated when the voltage across the active and return electrodes 206,207 is greater than a predetermined level.

FIG. 7 shows another embodiment of a voltage indicator circuit 200'''. A signal generator 202 is in circuit with electrodes 206,207 and a transformer circuit 240 connected in parallel with the electrodes. The transformer circuit 240 includes transformer 242 having a first winding 244 coupled to the electrodes 206,207 and a second winding 246 having series coupled series resistor 216 and neon bulb 218 coupled there across. The step-up transformer 242 allows a range of thresholds at which the bulb 218 is illuminated.

Figure 8:
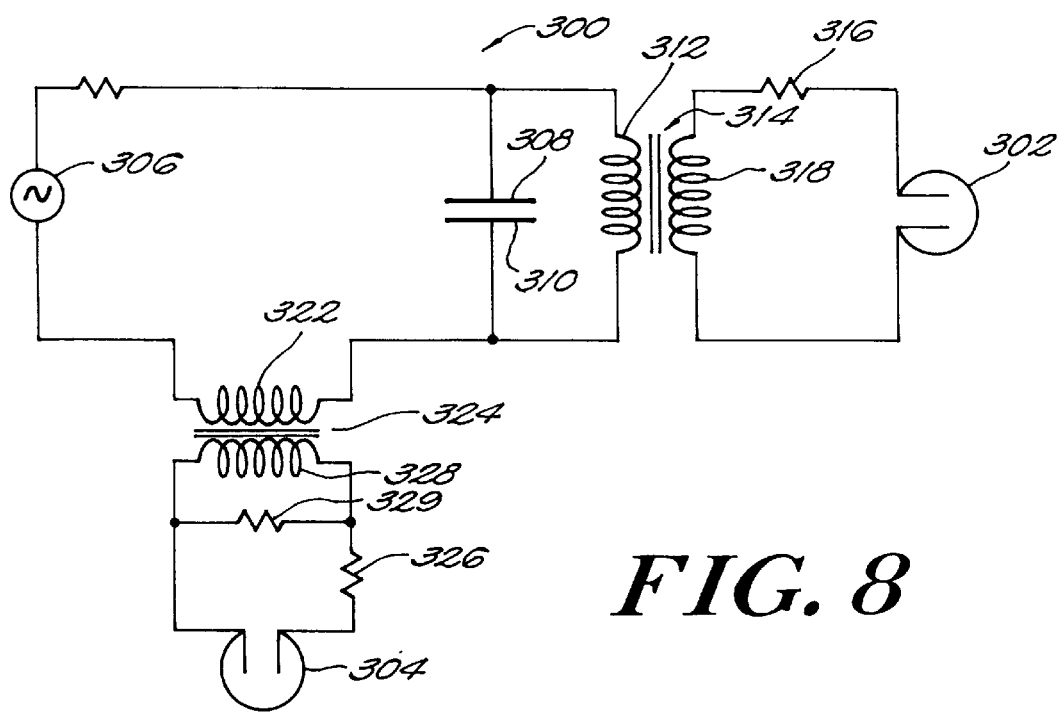
FIG. 8 is a schematic diagram of another embodiment of the indicator circuit of FIG. 4.

In another embodiment shown in FIG. 8, an indicator circuit 300 includes a first lamp 302 illuminated when a voltage across a tissue load is greater than a predetermined level and a second lamp 304 illuminated when a current through the tissue load is greater than a predetermined level. The indicator circuit 300 includes a signal generator 306 for energizing electrodes 308,310 which are connected to a first winding 312 of a transformer 314 and a series coupled series resistor 316 and first lamp 302 connected across a second winding 318 of the transformer. When a voltage across the electrodes is greater than a predetermined threshold, the first lamp 302 illuminates.

The indicator circuit 300 further includes a first winding 322 of a second transformer 324 and a second lamp 304 connected to a second winding 328 of the transformer 324. An optional ballast resistor 329 is coupled to the second winding 328. When a current through the electrodes 308,310 is greater than a predetermined threshold, the second lamp 304 illuminates.

The first and second lamps 302,304 of FIG. 8 provide information with respect to the affected tissue area as indicated in Table 1. As shown in Table 1, both the current indicator lamp and the voltage indicator lamp are illuminated during efficient cutting and coagulation of tissue. After both current and voltage lamps have been on, the current indicator lamp goes off to indicate that coagulation is complete.

TABLE 1

| Current Indicator | Voltage Indicator | |
|---|---|---|
| OFF | OFF | power off |
| ON | OFF | short circuit, i.e., too much tissue between the electrodes |
| ON | ON | tissue being affected |
| ON then OFF | ON | coagulation complete |
| OFF | ON | open circuit, i.e., no tissue in between the electrodes |

Information with respect to current and voltage being delivered to a tissue area by an electrosurgical tool enables a user to effectively cut and cauterize the tissue during a surgical procedure. The current and voltage indicator lamps provide real time information with respect to the tissue that is readily seen and understood by the user.

Figure 9:
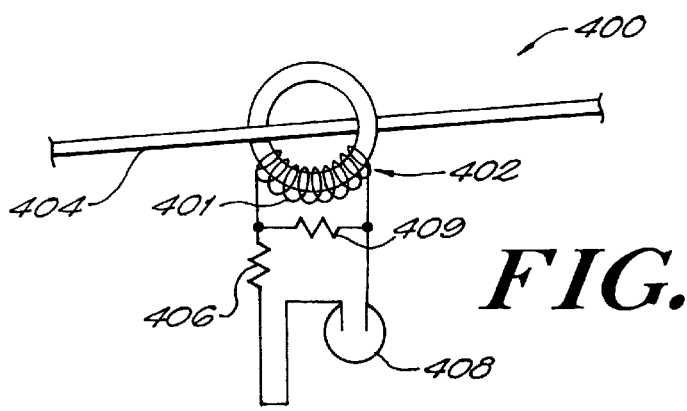
FIG. 9 is a schematic diagram of another embodiment of an indicator circuit in accordance with the invention adapted for use with a monopolar electrosurgical device.

In a further embodiment, a visual indicator circuit 400 for a monopolar device is shown in FIG. 9. In an exemplary embodiment, the indicator circuit 400 includes a toroid type transformer 402 having a wire 404 in spaced relation therethrough and carrying RF current from a signal generator (not shown). The transformer 402 includes a secondary 401 coupled in series with series resistor 406 and a type NE-2 neon bulb 408. An optional ballast resistor 409 is coupled to the secondary 401. In an illustrative embodiment, the neon bulb 408 has an illumination threshold of 60 V a.c. at 60 Hz, the series resistor is 200 k, wherein the threshold of illumination for the neon bulb is about 150 mA rms.

The circuit 400 of FIG. 9 can be mounted on a circuit board, or other means known to one skilled in the art, which includes a hole through which the wire passes. The series resistor could be soldered on, pushed on or an insulation displacement connector could be used. The transformer can be a split bobbin transformer which is snapped together. It will be appreciated that the circuit 400 could be located at various places within an instrument which are clearly visible to a user.

In an illustrative electrosurgical instrument, one of the described indicator circuits is located near an end effector of an electrosurgical tool such as the tool of FIG. 2 or 3. The end effector provides a location that is easily seen by a user of the tool without loss of focus on the area of affected tissue. The user need not look away from the tissue area for any measurable length of time as is needed to view a bar graph or other such display. Locating the indicator circuit, or lamp, near the end effector of an endoscope or laparoscopic instrument allows a surgeon to observe the lamp on a video monitor without diverting attention from the treatment site.

Other alternatives and modifications to the embodiments disclosed herein are possible. For example, the above-described circuit embodiments are illustrative and not intended as limiting the invention thereto. Further, other embodiments include multi-polar and multi-phasic electrosurgical systems which include the above-described circuits or variations thereof.

One skilled in that art will realize further features and advantages of the invention from the above-described embodiments. Accordingly, the invention is not to be limited by what has been particularly shown and described, except as indicated by the appended claims.

What is claimed is:

1. A bipolar electrosurgical system having a visual indicator, comprising:

an active electrode coupled to a power supply;

a return electrode electrically separated from the active electrode, the return electrode being adapted to receive electrosurgical energy from the active electrode;

a lamp in electrical communication with the active and return electrodes, wherein the lamp is illuminated when the electrosurgical energy exceeds a predetermined thresholds;

a sense resistor coupled in series with the active and return electrodes; and a transformer having a first winding coupled in parallel with the sense resistor and a second winding directly coupled to the lamp.

2. The electrosurgical system according to claim 1, wherein the lamp is a type NE-2 neon bulb.

3. The electrosurgical system according to claim 1, wherein the predetermined threshold is associated with the completion of tissue coagulation.

4. A bipolar electrosurgical system having a visual indicator, comprising:

an active electrode coupled to a power supply;

a return electrode electrically separated from the active electrode, the return electrode being adapted to receive electrosurgical energy from the active electrode;

a lamp in electrical communication with the active and return electrodes, wherein the lamp is illuminated when the electrosurgical energy exceeds a predetermined threshold; and a transformer having a first winding coupled in series with the active and return electrodes and a second winding coupled to a lamp resistor which is coupled in series with the lamp.

5. The electrosurgical system according to claim 4, further including at least one voltage protector connected in parallel with the lamp.

6. The electrosurgical system according to claim 5, wherein the at least one voltage protector prevents saturation of the transformer.

7. A bipolar electrosurgical system having a visual indicator, comprising:

an active electrode coupled to a power supply;

a return electrode electrically separated from the active electrode, the return electrode being adapted to receive electrosurgical energy from the active electrode; and a lamp in electrical communication with the active and return electrodes, wherein the lamp is illuminated when the electrosurgical energy exceeds a predetermined threshold; and a series resistor coupled in series with the lamp, wherein the series connected lamp and series resistor are coupled in parallel with the active and return electrodes.

8. A bipolar electrosurgical system having a visual indicator, comprising:

an active electrode coupled to a power supply;

a return electrode electrically separated from the active electrode, the return electrode being adapted to receive electrosurgical energy from the active electrode; and a lamp in electrical communication with the active and return electrodes, wherein the lamp is illuminated when the electrosurgical energy exceeds a predetermined threshold; and a transformer having a first winding coupled in parallel with the active and return electrodes and a second winding coupled to the lamp.

9. The electrosurgical system according to claim 1, wherein the electrosurgical energy is current and further including a further lamp in electrical communication with the active and return electrodes, wherein the further lamp is illuminated when a voltage present in the tissue is greater than a predetermined level.

10. The electrosurgical system according to claim 1, wherein the electrosurgical system is an impedance feedback electrosurgical system.

11. An electrosurgical system including a visual indicator for detecting and indicating electrosurgical energy flow through a tissue area, comprising:

an active electrode for delivering the electrosurgical energy;

a return electrode for receiving a current from the active electrode;

a transformer having a first winding coupled to the return electrode and a second winding; and a first NE-2 type neon bulb, the neon bulb being coupled to the second winding of the transformer and illuminated when the current is greater than a predetermined threshold.

12. The electrosurgical system according to claim 11, further including a second type NE-2 neon bulb, wherein the second neon bulb is illuminated by a voltage present across the active and return electrodes greater than a predetermined threshold.

13. The electrosurgical system according to claim 11, further including a sense resistor connected to the first winding of the transformer.

14. An electrosurgical device including a visual indicator circuit for indicating electrosurgical energy is present in an area of affected tissue, the electrosurgical device comprising:

a toroid type transformer having a secondary winding;

a wire for carrying current extending through the transformer to the tissue, the wire being in spaced relation with respect to the toroid transformer; and a type NE-2 neon bulb coupled in series with the series resistor, the series-coupled bulb and series resistor being directly coupled to the secondary winding of the transformer, wherein the lamp is illuminated when the current through the wire is greater than a predetermined threshold.

15. The electrosurgical device according to claim 14, wherein the electrosurgical device is monopolar.

16. An impedance feedback electrosurgical system for maintaining an impedance of a tissue area within a predetermined range while applying electrosurgical energy including a visual indicator, the electrosurgical system comprising:

a first electrode in electrical connection with a power supply for energizing the first electrode;

a second electrode located in proximity with respect to the first electrode;

a first lamp illuminated when a current flowing between the first and second electrodes is greater than a predetermined level; and a second lamp illuminated when a voltage between the first and second electrodes is greater than a predetermined level.

17. A method of monitoring the treatment of tissue with an electrosurgical instrument comprising the steps of:

providing an electrosurgical tool including a current indicating circuit having first and second lamps in electrical communication with a pair of electrodes for treating the tissue, the pair of electrodes being energized by a power supply, the first lamp being illuminated when a current through the tissue is greater than a predetermined current threshold and the second lamp being illuminated when a voltage across the tissue is treater than a predetermined voltage threshold;

applying electrosurgical energy to the tissue at an electrosurgical energy level sufficient to cause the first and second lamps to be illuminated;

visually monitoring the status of the first and second lamps; and discontinuing the application of electrosurgical energy to the tissue when the first lamp is not illuminated.

18. The method according to claim 17, wherein the first lamp is a type NE-2 neon lamp.

\* \* \* \* \*

UNITED STATES PATENT AND TRADEMARK OFFICE
CERTIFICATE OF CORRECTION

PATENT NO. : 5,817,091
DATED : October 6, 1998
INVENTOR(S) : Nardella et al.

It is certified that error appears in the above-identified patent and that said Letters Patent is hereby corrected as shown below:

| Column | Line(s) |  | Should read |
|---|---|---|---|
| 5 | 58 | oil | il |
| 5 | 65 | oil | il |
| 6 | 29-30 | pertinacity | permativity |
| 8 | 29 | thresholds | threshold |
| 10 | 42 | treater | greater |

Signed and Sealed this

Twenty-eighth Day of March, 2000

Attest:

Attesting Officer

Q. TODD DICKINSON

Commissioner of Patents and Trademarks